United States Patent [19]
Franz et al.

[11] Patent Number: 5,928,943
[45] Date of Patent: Jul. 27, 1999

[54] EMBRYONAL CARDIAC MUSCLE CELLS, THEIR PREPARATION AND THEIR USE

[75] Inventors: Wolfgang-Michael Franz, Gross Grönau; Anna M. Wobus, Gatersleben, both of Germany

[73] Assignee: Institut für Pflanzengenetik und Kulturpflanzenforschung, Gatersieben, Germany

[21] Appl. No.: 08/849,706

[22] PCT Filed: Nov. 21, 1995

[86] PCT No.: PCT/DE95/01699

§ 371 Date: Aug. 22, 1997

§ 102(e) Date: Aug. 22, 1997

[87] PCT Pub. No.: WO96/16163

PCT Pub. Date: May 30, 1996

[30] Foreign Application Priority Data

Nov. 22, 1994 [DE] Germany .............................. 44 41 327

[51] Int. Cl.[6] .............................. C12N 5/06; C12N 5/10; C12N 5/16; C12Q 1/02
[52] U.S. Cl. .............................. 435/363; 435/29; 435/34; 435/325; 435/366; 435/375
[58] Field of Search .............................. 435/325, 29, 363, 435/34, 366, 375; 514/44

[56] References Cited

FOREIGN PATENT DOCUMENTS

93/12233   6/1993   WIPO .

OTHER PUBLICATIONS

Arnold et al. "Cloning, Partial Sequencing & Expression of Glyceraldehyde–3–Phosphate Dehydrogenase Gene . . . " JBC 257(16) 9872–9877, 1982.

Orkin et al. "Report & Recommendations of the Panel to Assess the NIH Investment in Research on Gene Therapy", 1995.

Wobus et al. Retinoic acid induces expression of the ventricular 2.1 kb myosin–light–chain–2 promoter during in vitro cardiogenesis of embryonic stem cells. Circulation. 92 (8 Suppl.): 1114, 1995.

Engelmann et al. Formation of fetal rat cardiac cell clones by retroviral transformation: Retention of select myocyte characteristics. J. Mol. Cell. Cardiol. 25 (2): 197–213, Feb. 1993.

Hunter et al. Ventricular expression of a MLC–2v–ras fusion gene induces cardiac hypertrophy and selective diastolic dysfunction in transgenic mice. J. Biol. Chem. 270 (39): 23173–23178, 1995.

Lee et al. Myosin light chain–2 luciferase transgenic mice reveal distinct regulatory programs for cardiac and skeletal muscle–specific expression of a single contractile protein gene. J. Biol. Chem. 267 (22): 15875–15885, 1992.

De Wet et al. Firefly luciferase gene: Structure and expression in mammalian cells. Mol. Cell. Biol. 7 (2): 725–737, 1987.

*Primary Examiner*—Nancy Degen
*Attorney, Agent, or Firm*—Horst M. Kasper

[57] ABSTRACT

The invention concerns embryonal (cardiomyocytary and cardiomyoblastary) cardiac muscle cells, their preparation and their use, in particular for cell-mediated gene transplant. The areas of application of the invention are medicine and genetic engineering. The embryonal cardiac muscle cells according to the invention contain two gene constructs comprising: a) a regulatory, 1.2-kb long DNA sequence of the ventricle-specific myosin light-chain-2 (MLC-2v) promoter, the selectable marker gene β-galactosidase in fusion with the reporter gene neomycin; and b) a regulatory DNA sequence of the herpes simplex virus thymidine kinase promoter and the selectable marker gene hygromycin, and optionally immortalizing genes and/or optionally genes inactivated by homologous recombination and/or optionally one or a plurality of therapeutic genes. The cells can advantageously be used for cell-mediated gene transplant, in particular for constructing healthy tissue and assisting contractile functions, for investigating substances, in particular for pharmacological investigations and for the transfer of therapeutic genes into the myocardium.

7 Claims, 2 Drawing Sheets

EMBRYONAL CARDIAC MUSCLE CELLS, THEIR PREPARATION AND THEIR USE

The invention relates to embryonal (cardiomyocytary and cardiomyoblastary) cardiac muscle cells, their preparation and their use, in particular for cell-mediated gene transplant. The areas of application of the invention are medicine and genetic engineering.

There are already several works which deal with cardiac muscle cell cultures of mammals. The first investigations were performed with primary cultures of embryonal, neonatal, or adult cardiac tissue. The use of permanent cell lines of cardiomyocytary tissue is more advantageous since in this case one can make available a larger amount of a homogeneous cell population of a defined level of development. For this reason, there existed a series of experiments for the immortalization of cardiac muscle cells (amongst others, A. Sen et al., J. Biol. Chem. 263/1988/, 19132–19136). However, all of the hitherto existing cell lines exhibit the disadvantage that functional defects become noticeable in case of a long-term cultivation.

It is the goal of the invention to obtain embryonal (cardiomyocytary and cardiomyoblastary, respectively) cardiac muscle cells starting from pluripotent embryonal stem cells (ESC) or primordial germ cells (EGC, Steward et al., Dev. Biol. 161/1994, 626–628) after their differentiation into spontaneously pulsatile cardiac cells, where said embryonal cardiac muscle cells exhibit substantially identical properties to the cardiac muscle tissue. These cells are to be suitable for a therapeutic application, possible after additional genetic-engineering change. The object of the invention is to construct a vector system for the modification of the stem cells and to develop a selection method for the transfected cells.

The invention is realized with modified embryonal stem cells according to claim 1 to 4, the vector systems according to claim 5 and 6, and the selection method according to claim 7. The use of the modified embryonal stem cells according to claim 8 to 10 also belongs to the scope of the protection of the invention.

The invention vectors comprise the following components:

a) the regulatory, 2.1-kb long DNA sequence of the ventricle-specific myosin light-chain-2(MLC-2v) as promoter, the selectable marker gene β-galactosidase and the reporter gene neomycin as fusion gene "βgeo" and the SV40-PolyA-Tail (pAA) and possibly a position for the receiving of immortalizing genes.

b) the regulatory DNA sequence of the herpes simplex virus thymidine kinase promoters (HSV-Tk), the selectable marker gene hygromycin, and the SV40-PolyA-Tail (pAA).

Pluripotent embryonal stem cells are transfected in vitro with these vectors. The successfully transfected cells are selected in a first step with the aid of hygromycin. Hygromycin-resistant cells are then differentiated to so-called embryoid bodies. Thereupon, a selection of the hygromycin-resistant embryoid bodies is made with the cytotoxin Geneticin (G418). The resulting cells are further cultured and investigated as to their composition (gene expression, proteins), their function, and their contractile properties.

Embryonal stem cells (ESC) or primordial germ cells (EGC) of different origin, amongst others, of a mouse, rat, pig, cattle, dog, rabbit, hamster, including human cells, can be employed as starting material.

The invention vectors and the course of the cell selection method are illustrated in FIG. 1.

A further object of the invention are cells, which contain in addition to the recited vectors a) and b) also therapeutic genes such as, for example, the angiogenesis factors VEGF or bFGF, which therapeutic genes are obtained by viral or non-viral gene transfer. The thus obtained cell lines can be employed—with or without viral sequences—for the cell-mediated gene transplant, in particular for constructing healthy tissue and assisting contractile functions.

A further important use of the invention cell lines is the in-vitro testing of biologically active substances, in particular for the investigation of pharmacologically relevant substances or for the determination of toxic effects of exogenic agents on cardiac cells in culture. Animal testing is thereby spared in particular in screening programs and, as a result, the urgent requirement by the public to find alternative methods to animal testing is fulfilled.

The cell lines can further serve as a vesicle for a local gene transfer into the myocardium. For this purpose, the desired therapeutic genes are transfected by a viral gene transfer process, preferably with an adenovirus or an adenovirus-associated virus shuttle vector, or by a non-viral gene transfer process. Preferably, the packing of the gene is carried out with the AAV vector pSub201.

Based on the invention it is possible for the first time to treat myocardial diseases with the aid of the cellular gene transfer (genetic engineering) This represents a substantial medical advance, in particular, also diseases such as ischaemic and congenital cardiomyopathy can be treated in the future with greater chances of success.

The invention is described in greater detail in the following based on execution examples.

1. Cloning of the Vectors for the Selection of Embryonal (cardiomyocytary and cardiomyoblastary) cardiac muscle cells The following elements are the starting point for the constitution of the vectors:

2.1 kb MLC-2v promoter (clonable with KpnI and EcoRI), fusion gene βgeo (clonable with BamHI), SV40-PolyA (clonable with SacI), and Tk-hygromycin fusion gene in the Bluescript KS vector. As illustrated in FIG. 1, two (2) vectors for the cotransfection in pluripotent embryonal stem cells are produced from these elements:

(A) 2.1 MLC-2v-βgeo (B) Tk hygromycin.

2. Cotransfection of the Vectors in Pluripotent Stem Cells (ES cells) and Selection with Hygromycin B Any ES cell line can be employed as pluripotent stem cell line, where the ES cell line differentiates in cardiomyocytes (Wobus et al., Differentiation 48/1991/, 173–182), for example, the line D3 (Doetschmann et al., J. Embryol. Exp. Morphol. 3/1985/, 27–45). The D3 cells are cultivated on gelatinized plates with standardized culture medium on feeder-layer or in the presence of the recombinants "Leukemia-Inhibiting-Factor" (LIF). The Leukemia-Inhibiting-Factor LIF corresponds to the "Differentiation Inhibiting Factor" which prevents the differentiation of the ES cells and promotes the cell division of the pluripotent ES cells. The DNA constructs illustrated in FIG. 1 are entered by way of electroporation into the ES cells. For this purpose, the vectors are linearized by means of restriction enzymes and are transfected in a concentration of 25 μg/ml by means of electroporation. Thereafter, the pluripotent ES cell lines are expanded in the LIF/ES cell medium. Only the thymidine kinase promoter is active in the non-differentiated ES cells, which leads to an expression of the hygromycin resistance gene. Based on the addition of hygromycin B, the ES cells are selected (positive selection) in regard to the incorporation of the foreign DNA.

3. Proof of the Integration of MLC-2v-/βgeo in ES cells and Embryoid Bodies

The differentiation system of the hanging drop is employed for the obtaining of embryoid bodies. In this case, a cell suspension, which contains about 400–600 ES cells in 20 μl, is pipetted onto the covers of Petri dishes, which are filled with a physiological buffer solution. The cells collect in the drop and form embryoid bodies after a two-day to three-day incubation. After seven days, the embryoid bodies are transferred to microtest tissue culture dishes, where they adhere to the gelatin-coated substrate. Different cell types grow during the subsequent cultivation, amongst others, cardiac muscle cells (FIG. 2). Two to ten days after placement onto the culture dishes, about 80 to 90% of the fully grown embryoid bodies contain colonies of spontaneously and synchronously contracting cardiac muscle cells (Wobus et al., 1991). The MLC-2v promoter is active in these embryonal cardiac muscle cells. The expression of the fusion gene β-galactosidase/neomycin occurs in case of a successful transfection and integration of the MLC-2v-βgeo vector in the genome of the ES cells. The cardiomyocytary cells, which are of clonal origin, can be identified by blue staining in the β-galactosidase assay.

4. Selection of Embryonal Cardiomyocytary and Cardiomyoblastary Cells

In a second step, the positive ES cell clones, which contain both the Tk-hygromycin as well as the MLC-2v-βgeo fusion gene, are again expanded and a part is brought under the above-described conditions to the differentiation in embryoid bodies. At the point in time of the cardiomyogenic differentiation in the embryoid body, the cytotoxin Geneticin (G418) in a concentration of 300 μg/ml is added to the embryoid bodies. Therewith, the embryonal (cardiomyocytary and cardiomyoblastary, respectively) cardiac muscle cells are selected at an early stage.

The obtained cells are investigated in regard to tissue-specific gene expression, functional properties with the aid of electrophysiological techniques, and in regard to their contractile properties, the composition of the contractile proteins is characterized with corresponding monoclonal antibodies. Within the framework of genetic engineering, dividable, pulsatile cells can be transferred in the following to adult and neonatal cardiomyopathic mdx-mice after thoracotomy and direct injection into the myocardium.

BRIEF DESCRIPTION OF THE FIGURES

Characterization of the Hyg and G418 resistant cells in regard to cardiomyocytary and cardiomyoblastary properties, respectively

↓

Figure 1:
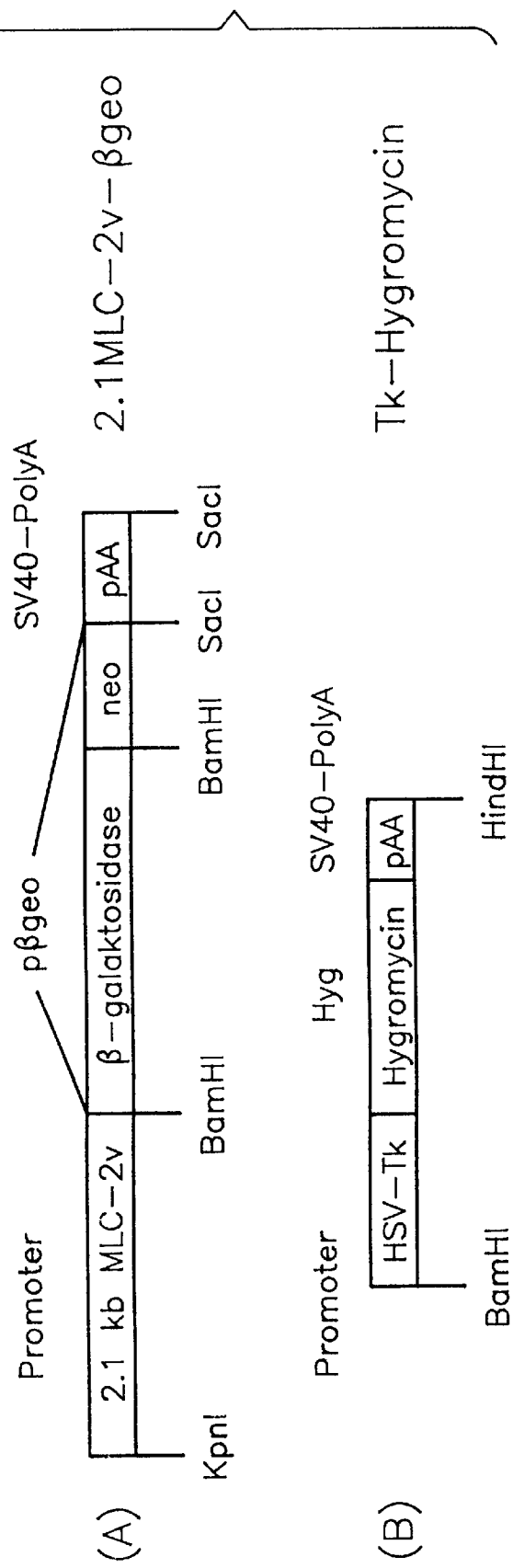
FIG. 1:
(C) Cotransfection of Tk-hygromycin and 2.1 MLC-2v-βgeo in ES(EG) cells
  Selection of the transfected ES(EG) cells
  Differentiation of the Hyg-resistant ES(EG) cells to embryoid bodies
  Selection of cardiac muscle cells out of embryoid bodies by means of G418
Figure 2:
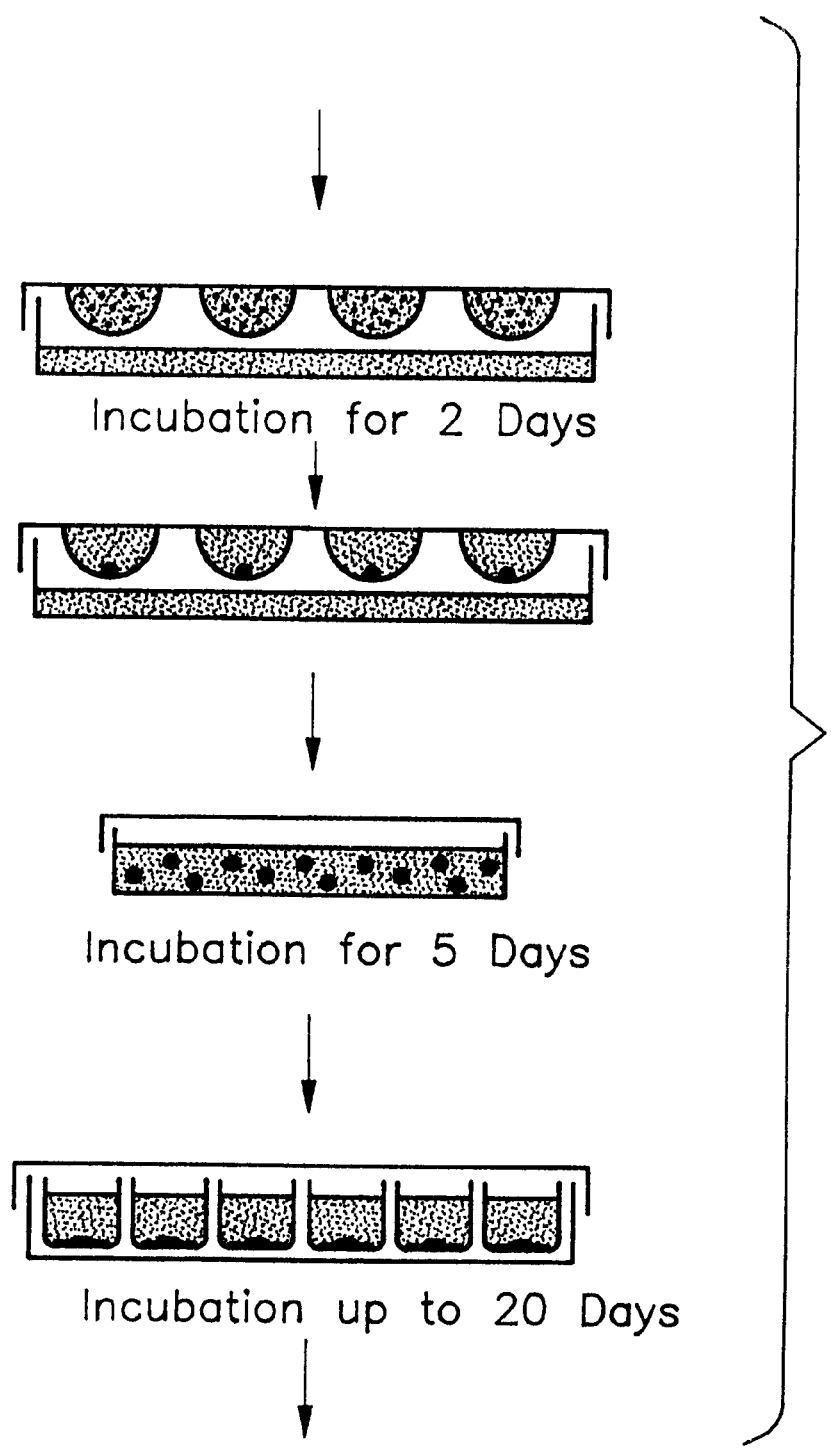
FIG. 2:
Embryonal stem cells cultivated on feeder layer
Cultivation of 400 or 600 cells/20 μl medium in hanging drops (incubation for 2 days)

Reaction of the embryoid bodies and cultivation in suspension (incubation for 5 days)

↓

Placing embryoid bodies on 24-well tissue culture plates (incubation up to 20 days)

↓

1. PCR Analysis
2. Enzymatic Dissociation of the Cardiomyocytes
3. Immunofluorescence
4. Patch-clamp Tests

We claim:

1. An embryonal cardiac muscle cell, essentially consisting of two gene constructs of two different regulatory DNA sequences and two different selectable marker genes.

2. The embryonal cardiac muscle cell according to claim 1, essentially consisting of two gene constructs comprising
   a) a regulatory, 2.1 kb long DNA sequence of the ventricle-specific myosin light-chain-2(MLC-2v) promoter, the selectable marker gene β-galactosidase, and the reporter gene neomycin, and
   b) a regulatory DNA sequence of the herpes simplex virus thymidine kinase promoter and the selectable marker gene hygromycin.

3. The embryonal cardiac muscle cell according to claim 1, further comprising sequences of the adenovirus (Ad) or of the adeno-associated virus (AAV).

4. A vector, comprising MLC-2 promoter, selectable marker gene β-galactosidase and the reporter gene neomycin as fusion gene "βgeo", and SV40-Poly A-Tail.

5. The vector according to claim 4, further comprising a position for receiving immortalizing genes.

6. A vector, essentially consisting of a regulatory DNA sequence of the herpes simplex virus thymidine kinase promoter and the selectable marker gene hygromycin.

7. A method for determining the effects of pharmacological substances comprising
   contacting pharmacological substances with embryonal cardiac muscle cells; and
   determining the effects of said substances on said cells.

* * * * *